(12) United States Patent
Müller et al.

(10) Patent No.: US 11,130,963 B2
(45) Date of Patent: Sep. 28, 2021

(54) TOMATO LEAF CURL NEW DELHI VIRUS (TOLCNDV) RESISTANT MELONS

(71) Applicant: RIJK ZWAAN ZAADTEELT EN ZAADHANDEL B.V., De Lier (NL)

(72) Inventors: Florian Müller, De Lier (NL); Daniël Johannes Wilhelmus Ludeking, De Lier (NL)

(73) Assignee: RIJK ZWAAN ZAADTEEL EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 16/691,059

(22) Filed: Nov. 21, 2019

(65) Prior Publication Data

US 2020/0131527 A1    Apr. 30, 2020

Related U.S. Application Data (63) Continuation-in-part of application No. PCT/EP2018/063924, filed on May 28, 2018.

(30) Foreign Application Priority Data

May 29, 2017  (EP) .................. PCT/EP2017/062923
Jun. 28, 2017  (EP) .................. PCT/EP2017/066024

(51) Int. Cl.
   *C12N 15/82*  (2006.01)
(52) U.S. Cl.
   CPC .............. *C12N 15/8283* (2013.01)
(58) Field of Classification Search
   None
   See application file for complete search history.

(56) References Cited

FOREIGN PATENT DOCUMENTS

| WO | 2004/101798 A2 | 11/2004 |
| WO | 2017/114848 A1 | 7/2017 |
| WO | 2017/186920 A1 | 11/2017 |

OTHER PUBLICATIONS

Carmelo Lopez, et al., Mechanical Transmission of Tomato Leaf Curl New Delhi Virus to Cucurbit Germplasm: Selection of Tolerance Sources in Cucumis Melo, Euphytica (2015) 204:679-691.
S. Yazdani-Khameneh, et al., Report of a New Begomovirus on Melon in Iran, New Disease Reports (2013) 28. 17. Published by the British Society for Plant Pathology [http://dx.doi.org/10.5197/j.2044-0588.2013.017].
Int'l Search Report and Written Opinion dated Jun. 29, 2018 in International Application PCT/EP2018/063924.

*Primary Examiner* — Brent T Page
(74) *Attorney, Agent, or Firm* — Duane Morris LLP; Thomas J. Kowalski; Deborah L. Lu

(57) ABSTRACT

The present invention relates to a cultivated melon (*Cucumis melo* spp. *melo*) plant resistant against Tomato Leaf Curl New Delhi virus (ToLCNDV), which comprises QTL-1 in its genome, and which QTL-1 confers resistance against Tomato Leaf Curl New Delhi virus (ToLCNDV). The invention further provides progeny, fruit, seeds, propagation material and food products from the plant. The invention also provides markers for the identification of QTL-1, as well as a method for testing a melon (*Cucumis melo* spp. *melo*) plant for the presence of QTL-1 in its genome and a method for selecting or identifying a melon plant resistant against ToLCNDV. Also provided is a method for producing a melon (*Cucumis melo* spp. *melo*) plant which is resistant against Tomato Leaf Curl New Delhi virus (ToLCNDV).

22 Claims, 4 Drawing Sheets

Specification includes a Sequence Listing.

SEQUENCE LISTING

```
<160> NUMBER OF SEQ ID NOS: 10

<210> SEQ ID NO 1
<211> LENGTH: 201
<212> TYPE: DNA
<213> ORGANISM: Cucumis melo

<400> SEQUENCE: 1
cttcttcttc ttcttcttct tcttcttcaa tggccttcaa atcatcctct gaagttttat      60
ccaccagtca ttccactggt aatacttcca acagcttaca ccatggaaga gaaattgaag     120
cgctaccgac ccctttccc aactttgatt tgggacccgt tccatcgcct ctagaagttg     180
aagctgcagt tgctgctctt c                                               201

<210> SEQ ID NO 2
<211> LENGTH: 201
<212> TYPE: DNA
<213> ORGANISM: Cucumis melo

<400> SEQUENCE: 2
cttcttcttc ttcttcttct tcttcttcaa tggccttcaa atcatcctct gaagttttat      60
ccaccagtca ttccactggt aatacttcca acagcttacg ccatggaaga gaaattgaag     120
cgctaccgac ccctttccc aactttgatt tgggacccgt tccatcgcct ctagaagttg     180
aagctgcagt tgctgctctt c                                               201

<210> SEQ ID NO 3
<211> LENGTH: 201
<212> TYPE: DNA
<213> ORGANISM: Cucumis melo

<400> SEQUENCE: 3
```
ttcatcaggg actttcttat atgaaagtaa ttaaagtctc tgtggtttgc aatctttttt            60
tcctatattt ttatgatcat cctacaagtt gctcatcaaa gggatcaaga aayggcagtg           120
tagatatcaa tttggatgga ggaagaatgt ggggtggcaa ctagaagaaa aaaaagaaaa           180
gctttgtata ttaaaaaata t                                                    201

<210> SEQ ID NO 4
<211> LENGTH: 201
<212> TYPE: DNA
<213> ORGANISM: Cucumis melo

<400> SEQUENCE: 4
ttcatcaggg actttcttat atgaaagtaa ttaaagtctc tgtggtttgc aatctttttt            60
tcctatattt ttatgatcat cctacaagtt gctcatcaaa aggatcaaga aayggcagtg           120
tagatatcaa tttggatgga ggaagaatgt ggggtggcaa ctagaagaaa aaaaagaaaa           180
gctttgtata ttaaaaaata t                                                    201

<210> SEQ ID NO 5
<211> LENGTH: 119
<212> TYPE: DNA
<213> ORGANISM: Cucumis melo

<400> SEQUENCE: 5
ttaatacgaa gaggagaagc tgttttatct taccaagccg atcaggatca ctgattgaaa            60
acccagtagc ctcgtcggtg atgtagacaa cagaagccat tcttgaatta tgagtccaa           119

<210> SEQ ID NO 6
<211> LENGTH: 119
<212> TYPE: DNA
<213> ORGANISM: Cucumis melo

<400> SEQUENCE: 6
ttaatacgaa gaggagaagc tgttttatct taccaagccg atcaggatca ctgattgata            60
acccagtagc ctcgtcggtg atgtagacaa cagaagccat tcttgaatta tgagtccaa           119

<210> SEQ ID NO 7
<211> LENGTH: 99
<212> TYPE: DNA
<213> ORGANISM: Cucumis melo
<220> FEATURE:
<221> NAME/KEY: misc_feature
<222> LOCATION: 40
<223> OTHER INFORMATION: /note="n = a or t or c or g"

<400> SEQUENCE: 7
ttaaatccag gatgaatttg tttagccttg agatgattan gagaagaact atatgttgtt            60
tttcacttca aggcttgtat ttttgcgttt ttttttttcc                                 99

<210> SEQ ID NO 8
<211> LENGTH: 99
<212> TYPE: DNA
<213> ORGANISM: Cucumis melo
<220> FEATURE:
<221> NAME/KEY: misc_feature
<222> LOCATION: 40
<223> OTHER INFORMATION: /note="n = a or t or c or g"

<400> SEQUENCE: 8
ttaaatccag gatgaatttg tttagccttg agatgattcn gagaagaact atatgttgtt            60

```
tttcacttca aggcttgtat ttttgcgttt tttttttcc                          99

<210> SEQ ID NO 9
<211> LENGTH: 121
<212> TYPE: DNA
<213> ORGANISM: Cucumis melo

<400> SEQUENCE: 9
aaaaatgtgt cggcggcatc aaagttccta tgagtttatg actagtaatc tttgcgtttg    60
gataaaatga gatctgaaaa cacctacakt gvawakkyrc vrmamamarg adayarrtct   120
a                                                                  121

<210> SEQ ID NO 10
<211> LENGTH: 121
<212> TYPE: DNA
<213> ORGANISM: Cucumis melo

<400> SEQUENCE: 10
aaaaatgtgt cggcggcatc aaagttccta tgagtttatg actagtaatc tttgcgtttg    60
aataaaatga gatctgaaaa cacctacakt gvawakkyrc vrmamamarg adayarrtct   120
a                                                                  121
```

TOMATO LEAF CURL NEW DELHI VIRUS (TOLCNDV) RESISTANT MELONS

RELATED APPLICATIONS AND INCORPORATION BY REFERENCE

This application is a continuation-in-part application of international patent application Serial No. PCT/EP2018/063924 filed 28 May 2018, which published as PCT Publication No. WO 2018/219861 on 6 Dec. 2018, which claims benefit of international patent applications Serial No. PCT/EP2017/062923 filed 29 May 2017 and Serial No. PCT/EP2017/066024 filed 28 Jun. 2017.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named 00436SL.txt and is 4 kbytes in size.

FIELD OF THE INVENTION

The present invention relates to a melon (*Cucumis melo* spp. *melo*) plant resistant against Tomato Leaf Curl New Delhi virus (ToLCNDV). The invention further relates to progeny, seed and fruit of the melon plant that is resistant against ToLCNDV, and to a food product which may comprise such melon fruit or part thereof. The invention also relates to propagation material suitable for producing the melon plant, to a marker for the identification of resistant melon plants, to use of the said marker to identify or develop a ToLCNDV resistant melon plant or other markers, to a method of testing a melon plant for the ToLCNDV resistance, and to a method for producing a ToLCNDV-resistant melon plant.

BACKGROUND OF THE INVENTION

Viruses are amongst the most destructive and most difficult to control pathogens affecting cultivated melons (*Cucumis melo* spp. *melo*). The changes in the physiology and metabolism of virus infected plants lead to significant commercial losses through the reduction in growth and yield, as well as causing the fruit to be unmarketable.

One such virus is the Tomato Leaf Curl New Delhi virus (ToLCNDV), which is a virus that was initially described in 1995. The virus has rapidly dispersed to various parts of the world and to a wide range of host species, including melon. ToLCNDV is a bi-partite begomovirus transmitted by whiteflies (*Bemisia tabaci*).

In melon, the symptoms of plants infected with ToLCNDV include: severe yellowing and mosaic of the leaves, leaf curling, vein swelling and plant stunting. Additionally, the resultant fruits have symptoms ranging from rough skin, longitudinal cracking, dehydration and speckling. If plants are infected with ToLCNDV at an early stage, they are severely stunted and fruit production is affected, if not suppressed.

With the emergence of new plant viruses such as ToLCNDV, preventing infections from occurring and spreading have become of utmost importance. Currently, control measures against ToLCNDV are limited and mainly rely on various cultural, phytosanitary and hygienic practices to control whiteflies, including biological control or chemical treatments of whiteflies, cultivation of plants under insect-proof greenhouses, and the elimination of infected plants.

Citation or identification of any document in this application is not an admission that such document is available as prior art to the present invention.

SUMMARY OF THE INVENTION

To date, no resistant or tolerant ToLCNDV melon cultivars have been described. It is the object of the present invention to provide a cultivated melon plant that is resistant to ToLCNDV. This object has been met by providing a melon plant that may comprise a QTL, indicated as QTL-1, which confers resistance to ToLCNDV. The melon plant of the invention is a cultivated melon plant and preferably an agronomically elite melon plant.

In the research that led to the present invention, novel melon plants were developed such that they are highly resistant against ToLCNDV. The resistance of the invention is controlled by QTL-1, the inheritance of which is consistent with that of a monogenic trait. Moreover, the resistance of the present invention caused by QTL-1 is inherited in a partially dominant manner. This means that the highest level of resistance against ToLCNDV is achieved when QTL-1 is present homozygously. The heterozygous presence of QTL-1 in the genome of a plant confers an intermediate level of resistance against ToLCNDV, such that this level of resistance is lower than that of a plant in which QTL-1 is homozygously present in its genome.

The present invention relates to a melon (*Cucumis melo* spp. *melo*) plant resistant against Tomato Leaf Curl New Delhi virus (ToLCNDV), wherein the plant may comprise QTL-1 in its genome, which QTL-1 confers resistance to Tomato Leaf Curl New Delhi virus (ToLCNDV) and is present in a plant grown from a seed deposited under NCIMB accession number 42705.

The invention also relates to a cultivated melon fruit harvested from a plant of the invention, wherein the melon fruit may comprise QTL-1 in its genome and the melon fruit is resistant against ToLCNDV.

The invention also relates to a melon seed which may comprise QTL-1 in its genome.

The invention further relates to a cultivated melon plant or a fruit or a seed which may comprise only one allele of QTL-1 (i.e. heterozygously) in its genome.

The invention further relates to a plant of the invention which may comprise QTL-1 either homozygously or heterozygously and is a plant of an inbred line, a hybrid, a doubled haploid, or a plant of a segregating population.

The invention further relates to melon (*Cucumis melo* spp. *melo*) plants of the invention that have acquired QTL-1 from a suitable source, either by conventional breeding, or genetic modification, in particular by cisgenesis or transgenesis.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of *Cucumis melo* EX7.001 comprising QTL-1 which confers resistance to ToLCNDV were deposited under accession number NCIMB 42705 on 14 Dec. 2016 with NCIMB Ltd. (Ferguson Building, Craibstone Estate, Bucksburn, Aberdeen, AB21 9YA). All seeds of the deposit comprise QTL-1 homozygously. Plants grown from these seeds are thus highly resistant against ToLCNDV.

The deposited seeds do not meet the DUS criteria which are required for obtaining plant variety protection, and can therefore not be considered to be plant varieties.

The Deposits with NCIMB Ltd., under deposit accession number 42705 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

The species *Cucumis melo* has taxonomically been classified in various ways over the years, for example using a division into subspecies *melo* and *agrestis* with further classification into varieties, wherein basically all cultivated melons belong to the ssp. *melo*. Another classification divides *C. melo* into seven taxonomic varieties, one of which combines all wild melon types (*C. melo* var. *agrestis*), and the other six include the cultivated melons. These six cultivated varieties are *cantalupensis, inodorus, flexuosus, conomon, dudaim*, and *momordica*. The cultivated netted melon types muskmelon and cantaloupe, which include for example Galia, Charentais, Ogen, and Eastern and Western shippers, in this classification belong to *C. melo* var. *cantalupensis*. The other main group of sweet melons, such as Honeydews, and Cassaba types (e.g. Piel de Sapo, Jaune Canari) belong to *C. melo* var. *inodorus*, which may comprise non-climacteric and generally less or non-aromatic melon types with a better shelf life than *cantalupensis*. A cultivated melon plant and the fruit that it bears thus may be classified as either *C. melo* ssp. *melo, C. melo* var. *cantalupensis, C. melo* var. *inodorus, C. melo* var. *flexuosus, C. melo* var. *conomon, C. melo* var. *dudaim*, or *C. melo* var. *momordica*. In the context of this invention, when referring to a melon plant or a melon, unless otherwise specified, is a cultivated melon plant or the melon fruit produced by a cultivated melon plant.

In the research that led to the present invention, novel melon plants were developed such that they are highly resistant against ToLCNDV. The resistance of the invention is controlled by QTL-1, the inheritance of which is consistent with that of a monogenic trait. Moreover, the resistance of the present invention caused by QTL-1 is inherited in a partially dominant manner. This means that the highest level of resistance against ToLCNDV is achieved when QTL-1 is present homozygously. The heterozygous presence of QTL-1 in the genome of a plant confers an intermediate level of resistance against ToLCNDV, such that this level of resistance is lower than that of a plant in which QTL-1 is homozygously present in its genome.

Since the inheritance of the resistance is comparable to that of a monogenic trait, this is highly advantageous in the breeding of melons because the resistance is high, can readily be incorporated into various cultivated melon types, and is directed against ToLCNDV which at the time of making the present invention is a relatively newly emergent pathogen of cultivated melons for which no resistance in cultivated melons is known to exist.

The present invention relates to a melon (*Cucumis melo* spp. *melo*) plant resistant against Tomato Leaf Curl New Delhi virus (ToLCNDV), wherein the plant may comprise QTL-1 in its genome, which QTL-1 confers resistance to Tomato Leaf Curl New Delhi virus (ToLCNDV) and is present in a plant grown from a seed deposited under NCIMB accession number 42705. The phrase "present in" may also mean "found in" or "contained in" or "obtainable from" (the genome of) plants grown from seeds of the deposit or the deposited seeds themselves. These phrases are intended to indicate that the QTL of the invention is the same or essentially the same as the QTL in the genome of the deposited material. The QTL need not be identical in sequence but has in any case to perform the same function in causing the resistance to ToLCNDV. In other words, the QTL may comprise polymorphisms (i.e. variation in sequence) as compared to the QTL of the invention, but these polymorphisms do not have any bearing on the function of the QTL in causing the resistance phenotype. This melon plant is referred to herein as "a plant of the invention".

The resistance to ToLCNDV as shown by a plant of the invention is also referred to herein as "the trait of the invention". Resistant plants of the invention are capable of producing normal cultivated melon fruits that do not exhibit ToLCNDV symptoms.

Based on differences in ToLCNDV symptoms presenting on melon plants or fruits exposed to ToLCNDV infection, a skilled person is able to visually assess for symptoms and relate these symptoms or a lack thereof, to whether a plant or fruit is resistant or susceptible to ToLCNDV. ToLCNDV symptoms on melon plants and melon fruits are described in Table 2 and Table 5, respectively, when measured under the conditions as described in Example 1. In general, resistant plants of the invention present no ToLCNDV symptoms or only some non-specific yellowing or minimal symptoms such as some yellowing spots on older leaves and less than 25% of the plant surface is affected. Melon fruits of the invention are in general symptomless such that they are not deformed and do not show lesions, or slight or deep net cracking.

The invention also relates to a cultivated melon fruit harvested from a plant of the invention, wherein the melon fruit may comprise QTL-1 in its genome and the melon fruit is resistant against ToLCNDV. This melon fruit is also referred to herein as "the fruit of the invention" or "the melon fruit of the invention".

The invention also relates to a melon seed which may comprise QTL-1 in its genome. This melon seed is also referred to herein as "the seed of the invention" or "the melon seed of the invention". A melon plant that is grown from this seed is a plant of the invention. The invention also relates to seeds produced by a plant of the invention. These seeds harbor QTL-1, and as such, a plant grown from said seed is a plant of the invention.

In one embodiment, the plant grown from the seed of the invention is resistant against ToLCNDV.

The invention further relates to a cultivated melon plant or a fruit or a seed which may comprise only one allele of QTL-1 (i.e. heterozygously) in its genome. A cultivated melon plant or fruit or seed which may comprise QTL-1 heterozygously in its genome has an intermediate level of resistance against ToLCNDV, such that this level of resistance is lower than that of a cultivated melon plant or fruit or seed in which QTL-1 is homozygously present in its genome. Such plant or fruit or seed can also be used as a source for development of a plant or fruit or seed which may comprise two alleles of QTL-1.

The term "an allele of QTL-1" as used herein is the version of QTL-1 that leads to resistance to ToLCNDV. The wildtype allele does not lead to the resistance. The presence of an allele of QTL-1 can suitably be identified using a marker as described herein. In a preferred embodiment QTL-1 is present in homozygous form (i.e. 2 alleles of QTL-1 are present).

The invention further relates to a plant of the invention which may comprise QTL-1 either homozygously or heterozygously and is a plant of an inbred line, a hybrid, a doubled haploid, or a plant of a segregating population.

The invention further relates to melon (*Cucumis melo* spp. *melo*) plants of the invention that have acquired QTL-1 from a suitable source, either by conventional breeding, or genetic modification, in particular by cisgenesis or transgenesis. Cisgenesis is a genetic modification of plants with a natural gene, encoding a (agricultural) trait from the crop plant itself or from a sexually compatible donor plant. Transgenesis is a genetic modification of a plant with a gene from a non-crossable species or with a synthetic gene.

In one embodiment, the source from which QTL-1 of the invention is acquired, is formed by plants grown from seeds of which a representative sample was deposited under accession number NCIMB 42705, or from the deposited seeds NCIMB 42705, or from sexual or vegetative descendants thereof, or from another source which may comprise QTL-1 as defined herein that leads to resistance to ToLCNDV, or from any combination of these sources.

In a preferred embodiment, the source from which QTL-1 of the invention is acquired is a cultivated non-transgenic *C. melo* plant. The source for acquiring QTL-1 of the invention, to obtain a plant of the invention having resistance to ToLCNDV, is suitably a melon (*Cucumis melo* spp. *melo*) plant that carries QTL-1 homozygously in its genome, as it is present in the genome of seeds deposited under NCIMB 42705, or alternatively from a plant of a *Cucumis* species that carries said QTL-1 and that can be crossed with *C. melo*, and in particular with *Cucumis melo* spp. *melo*. When a *Cucumis* species other than *C. melo* is used as the source of QTL-1 of the invention, optionally, techniques such as embryo rescue, backcrossing, or other techniques that are known to the skilled person may be employed to obtain seed of the interspecific cross, which seed may be used as the source for further development of a cultivated non-transgenic *C. melo* plant that exhibits resistance to ToLCNDV.

To obtain QTL-1 from a source in which it is heterozygously present, a seed of such a plant may be grown and flowers pollinated with pollen from the same plant or from another plant that also has QTL-1 heterozygously to obtain a fruit with seeds. When these seeds are sown, the resulting plants will segregate according to normal segregation ratios, which means about 25% of the plants will have QTL-1 homozygously present, about 50% of the plants will have QTL-1 heterozygously present, and about 25% of the plants will not have QTL-1. For selection of a preferred plant having QTL-1 either homozygously or heterozygously, the presence of QTL-1 can suitably be determined using the markers as described herein. Alternatively, plants can be phenotypically observed and visually selected for the presence of resistance to ToLCNDV. The skilled person is aware of how to work with QTLs in heterozygous and homozygous form using known breeding and selection procedures.

Preferably, the plant of the invention is a non-transgenic plant.

QTL mapping studies were performed to identify the genetic region that is responsible for the trait of the invention, namely resistance to ToLCNDV. In these studies, a QTL designated QTL-1 was identified on chromosome 11. QTL-1 is flanked by markers having SEQ ID NO: 1 and SEQ ID NO: 9, which denotes the position on chromosome 11 between which QTL-1 is located (Table 1). In addition to flanking QTL-1, markers having SEQ ID NO: 1 and SEQ ID NO: 9 are linked to QTL-1. Markers having SEQ ID NO: 3, SEQ ID NO: 5 and SEQ ID NO: 7 have also been found to be linked to QTL-1 based on the QTL mapping studies performed here in. When the sequence of these markers are positioned on the publicly available genome reference sequence for *C. melo*, based on *C. melo* line DHL92 version 3.5 (Garcia-Mas et al. PNAS Vol. 109(29):11872-11877, 2012), the physical position to which the SNP polymorphism in said marker sequence corresponds is also indicated in Table 1. The position of QTL-1 is therefore also derivable from this public map and is relative to said physical positions. The latest version of the public *C. melo* genome reference sequence that is used herein is DHL92 version 3.5 and this data can for example be accessed at melonomics.net.

TABLE 1

Sequence data and the genetic and physical positions of the SNP markers. Polymorphic SNPs between the markers used to identify QTL-1 (bold and underlined) and that of the corresponding ToLCNDV susceptible wildtype melon sequence (underlined) are indicated.

| Marker name | Genetic position | Physical position of the SNP (based on the public genome DHL92 genome v.3.5) | Marker Sequence |
| --- | --- | --- | --- |
| SEQ ID NO. 1 | 93.85 cM | 28999728 bp | CTTCTTCTTCTTCTTCTTCTTCTTCTTCAATG GCCTTCAAATCATCCTCTGAAGTTTTATCCA CCAGTCATTCCACTGGTAATACTTCCAACA GCTTACACCATGGAAGAGAAATTGAAGCGC TACCGACCCCTTTTCCCAACTTTGATTTGGG ACCCGTTCCATCGCCTCTAGAAGTTGAAGC TGCAGTTGCTGCTCTTC |
| SEQ ID NO. 2 | 93.85 cM | 28999728 bp | CTTCTTCTTCTTCTTCTTCTTCTTCTTCAATG GCCTTCAAATCATCCTCTGAAGTTTTATCCA CCAGTCATTCCACTGGTAATACTTCCAACA GCTTACGCCATGGAAGAGAAATTGAAGCGC TACCGACCCCTTTTCCCAACTTTGATTTGGG ACCCGTTCCATCGCCTCTAGAAGTTGAAGC TGCAGTTGCTGCTCTTC |
| SEQ ID NO. 3 | 99.83 cM | 29694216 bp | TTCATCAGGGACTTTCTTATATGAAAGTAAT TAAAGTCTCTGTGGTTTGCAATCTTTTTTC CTATATTTTTATGATCATCCTACAAGTTGCT CATCAAAGGGATCAAGAAAYGGCAGTGTAG GATATCAATTTGGATGGAGGAAGAATGTGG GGTGGCAACTAGAAGAAAAAAAAGAAAAG CTTTGTATATTAAAAAATAT |
| SEQ ID NO. 4 | 99.83 cM | 29694216 bp | TTCATCAGGGACTTTCTTATATGAAAGTAAT TAAAGTCTCTGTGGTTTGCAATCTTTTTTC CTATATTTTTATGATCATCCTACAAGTTGCT CATCAAAAGGATCAAGAAAYGGCAGTGTA GATATCAATTTGGATGGAGGAAGAATGTGG GGTGGCAACTAGAAGAAAAAAAAGAAAAG CTTTGTATATTAAAAAATAT |
| SEQ ID NO. 5 | 102.06 cM | 29913499 bp | TTAATACGAAGAGGAGAAGCTGTTTTATCT TACCAAGCCGATCAGGATCACTGATTGAAA ACCCAGTAGCCTCGTCGGTGATGTAGACAA CAGAAGCCATTCTTGAATTATGAGTCCAA |
| SEQ ID NO. 6 | 102.06 cM | 29913499 bp | TTAATACGAAGAGGAGAAGCTGTTTTATCT TACCAAGCCGATCAGGATCACTGATTGATA ACCCAGTAGCCTCGTCGGTGATGTAGACAA CAGAAGCCATTCTTGAATTATGAGTCCAA |
| SEQ ID NO. 7 | 111.42 cM | 30844507 bp | TTAAATCCAGGATGAATTTGTTTAGCCTTGA GATGATTANGAGAAGAACTATATGTTGTTT TCACTTCAAGGCTTGTATTTTTGCGTTTTTT TTTTCC |
| SEQ ID NO. 8 | 111.42 cM | 30844507 bp | TTAAATCCAGGATGAATTTGTTTAGCCTTGA GATGATTCNGAGAAGAACTATATGTTGTTT TCACTTCAAGGCTTGTATTTTTGCGTTTTTT TTTTCC |

TABLE 1-continued

Sequence data and the genetic and physical positions of the SNP markers. Polymorphic SNPs between the markers used to identify QTL-1 (bold and underlined) and that of the corresponding ToLCNDV susceptible wildtype melon sequence (underlined) are indicated.

| Marker name | Genetic position | Physical position of the SNP (based on the public genome DHL92 genome v.3.5) | Marker Sequence |
|---|---|---|---|
| SEQ ID NO. 9 | 113.49 cM | 31270779 bp | AAAAATGTGTCGGCGGCATCAAAGTTCCTA TGAGTTTATGACTAGTAATCTTTGCGTTTG ATAAAATGAGATCTGAAAACACCTACAKTG VAWAKKYRCVRMAMAMARGADAYARRTC TA |
| SEQ ID NO. 10 | 113.49 | 31270779 bp | AAAAATGTGTCGGCGGCATCAAAGTTCCTA TGAGTTTATGACTAGTAATCTTTGCGTTTG<u>A</u> ATAAAATGAGATCTGAAAACACCTACAKTG VAWAKKYRCVRMAMAMARGADAYARRTC TA |

In one embodiment of the invention, QTL-1 is located on chromosome 11, between marker sequences SEQ ID NO: 1 and SEQ ID NO: 9. In particular, in the deposit with NCIMB accession number 42705, QTL-1 which confers resistance to ToLCNDV is located on chromosome 11, between marker sequences SEQ ID NO: 1 and SEQ ID NO: 9.

In one embodiment of the invention, QTL-1 is linked to one or more markers selected from the group consisting of SEQ ID NO: 1, SEQ ID NO: 3, SEQ ID NO: 5, SEQ ID NO: 7, and SEQ ID NO: 9, or any combination thereof.

In one embodiment of the invention, QTL-1 can be identified by one or more markers selected from the group consisting of SEQ ID NO: 1, SEQ ID NO: 3, SEQ ID NO: 5, SEQ ID NO: 7, and SEQ ID NO: 9, or any combination thereof.

In one embodiment of the invention, QTL-1 may comprise markers SEQ ID NO: 1, SEQ ID NO: 3, SEQ ID NO: 5, SEQ ID NO: 7, and/or SEQ ID NO: 9, more preferably QTL-1 may comprise markers SEQ ID NO: 3, SEQ ID NO: 5, and/or SEQ ID NO: 7, and most preferably QTL-1 may comprise marker SEQ ID NO: 5. In particular, in the deposit with NCIMB accession number 42705, QTL-1 which confers resistance to ToLCNDV and is located on chromosome 11, may comprise markers SEQ ID NO: 3, SEQ ID NO: 5, and SEQ ID NO: 7.

Moreover, the invention also relates to a food product or a processed food product which may comprise the melon fruit of the invention or part thereof. The food product may have undergone one or more processing steps. Such a processing step might comprise but is not limited to any one of the following treatments or combinations thereof: peeling, cutting, washing, juicing, cooking, cooling or preparing a salad mixture which may comprise the fruit of the invention. The processed form that is obtained is also part of this invention.

The invention also relates to propagation material suitable for producing a melon (*Cucumis melo* spp. *Melo*) plant of the invention, wherein the propagation material is suitable for sexual reproduction, and is in particular selected from a microspores, pollen, ovary, ovule, embryo sac and egg cell, or is suitable for vegetative reproduction, and is in particular selected from a cutting, root, stems cell, protoplast, or is suitable for tissue cultures of regenerable cells, and is in particular selected from a leaf, pollen, embryo, cotyledon, hypocotyl, meristematic cell, root, root tip, anther, flower, seed and stem, and wherein the plant produced from the propagation material may comprise QTL-1 that confers resistance to ToLCNDV. A plant of the invention may be used as a source of the propagation material.

The invention also relates to a cell of a melon (*Cucumis melo* spp. *melo*) plant resistant to ToLCNDV, which cell may comprise in its genome QTL-1, which QTL is located on chromosome 11, between SEQ ID NO: 1 and SEQ ID NO: 9, and which QTL is identified by or linked to or may comprise one or more markers selected from the group consisting of SEQ ID NO: 1, SEQ ID NO: 3, SEQ ID NO: 5, SEQ ID NO: 7, and SEQ ID NO: 9, or any combination thereof. Such a cell may either be in isolated form or a part of the complete plant or parts thereof and still constitutes a cell of the invention because such a cell harbours the genetic information that leads to the resistance to ToLCNDV of a cultivated melon plant. Each cell of a plant of the invention carries the genetic information that leads to resistance to ToLCNDV. A cell of the invention may also be a regenerable cell that can regenerate into a new plant of the invention. The presence of genetic information as used herein is the presence of QTL-1 as defined herein.

The invention further relates to plant tissue of a plant of the invention. The tissue can be undifferentiated tissue or already differentiated tissue. Undifferentiated tissues are for example stem tips, anthers, petals, pollen and can be used in micropropagation to obtain new plantlets that are grown into new plants of the invention. The tissue can also be grown from a cell of the invention.

The invention moreover relates to progeny of plants, cells, tissues and seeds of the invention, which progeny may comprise QTL-1 that leads to resistance to ToLCNDV. Such progeny can in itself be plants, cells, tissues, or seeds.

As used herein "progeny" is intended to mean the first and all further descendants from a cross with a plant of the invention.

"Progeny" also encompasses melon plants that carry QTL-1 of the invention and have the trait of the invention, and are obtained from other plants, or progeny of plants, of the invention by vegetative propagation or multiplication. Progeny of the invention comprise QTL-1 and show resistance to ToLCNDV.

The invention further relates to parts of a melon plant of the invention that are suitable for sexual reproduction. Such parts are for example selected from the group consisting of microspores, pollen, ovaries, ovules, embryo sacs, and egg cells. Additionally, the invention relates to parts of a melon plant of the invention that are suitable for vegetative reproduction, which are in particular cuttings, roots, stems, cells, protoplasts. The parts of the plants as previously mentioned are considered propagation material. The plant that is produced from the propagation material may comprise QTL-1 that leads to resistance to ToLCNDV.

The invention also relates to a tissue culture of a melon (*Cucumis melo* spp. *melo*) plant resistant to ToLCNDV, which tissue culture may comprise QTL-1, which QTL-1 is located on chromosome 11, between SEQ ID NO: 1 and SEQ ID NO: 9, and which QTL is identified by or linked to or may comprise one or more markers selected from the group consisting of SEQ ID NO: 1, SEQ ID NO: 3, SEQ ID NO: 5, SEQ ID NO: 7, and SEQ ID NO: 9, or any combination thereof. The tissue culture may comprise regenerable cells. Such tissue culture can be selected or derived from any part of the plant, in particular from leaves, pollen, embryos, cotyledon, hypocotyls, meristematic cells, roots, root tips, anthers, flowers, seeds, and stems. The tissue culture can be regenerated into a melon plant which may comprise QTL-1, wherein the regenerated melon plant expresses the trait of the invention and is also part of the invention.

The invention further relates to the germplasm of plants of the invention. The germplasm is constituted by all inherited characteristics of an organism and according to the invention encompasses at least the trait of the invention. The germplasm can be used in a breeding program for the development of cultivated *C. melo* plants having resistance to ToLCNDV. The use of germplasm that may comprise QTL-1 leading to the resistance to ToLCNDV in breeding is also part of the present invention.

The invention additionally relates to the use of a plant of the invention in plant breeding. The invention thus also relates to a breeding method for the development of cultivated melon plants that are resistant against ToLCNDV wherein germplasm which may comprise said resistance is used. Seed being representative for the germplasm was deposited with the NCIMB under accession number NCIMB 42705.

The invention also concerns the use of QTL-1 leading to the trait of the invention for the development of melon (*Cucumis melo* spp. *melo*) plants that have resistance to ToLCNDV.

The presence of the resistance conferring QTL-1 can be identified by a number of markers that are linked to QTL-1. The actual markers that are informative can depend on the background of the population that is observed, since polymorphisms can vary between genotypes. A marker that can identify QTL-1 is a marker linked to QTL-1 in a certain population. Markers found to be linked to QTL-1 are the markers the sequences of which are shown as SEQ ID NO: 1, SEQ ID NO: 3, SEQ ID NO: 5, SEQ ID NO: 7, and SEQ ID NO: 9.

The invention therefore also relates to a marker for the identification of QTL-1, wherein QTL-1 when present in the genome of a melon (*Cucumis melo* spp. *melo*) plant confers resistance to ToLCNDV, which marker is selected from the group consisting of SEQ ID NO: 1, SEQ ID NO: 3, SEQ ID NO: 5, SEQ ID NO: 7, and SEQ ID NO: 9, or any combination thereof. All these markers can also be used to develop other markers for the identification of QTL-1.

The invention also relates to use of a marker selected from the group consisting of SEQ ID NO: 1, SEQ ID NO: 3, SEQ ID NO: 5, SEQ ID NO: 7, and SEQ ID NO: 9, or any combination thereof, to identify or develop a ToLCNDV resistant melon (*Cucumis melo* spp. *melo*) plant, or develop additional marker(s) linked to QTL-1, which when present in the genome of a melon (*Cucumis melo* spp. *melo*) plant confers resistance to ToLCNDV.

The invention also relates to a method of testing a melon (*Cucumis melo* spp. *melo*) plant for the presence of QTL-1 in its genome, which may comprise detecting a marker sequence selected from the group consisting of SEQ ID NO: 1, SEQ ID NO: 3, SEQ ID NO: 5, SEQ ID NO: 7, and SEQ ID NO: 9, or any combination thereof, in the genome of the melon (*Cucumis melo* spp. *melo*) plant.

In one embodiment of the invention, the method of testing a melon (*Cucumis melo* spp. *melo*) plant for the presence of QTL-1 in its genome further may comprise selecting a melon (*Cucumis melo* spp. *melo*) plant that may comprise QTL-1 in its genome.

The invention also relates a method for identifying or selecting a melon (*Cucumis melo* spp. *melo*) plant resistant against Tomato Leaf Curl New Dehli virus (ToLCNDV), said method which may comprise:

a) assaying genomic nucleic acids of a melon (*Cucumis melo* spp. *melo*) plant for the presence of a genomic marker genetically linked to QTL-1, wherein QTL-1 is associated with ToLCNDV resistance, wherein said genomic marker is within 20 cM or 10 cM or 5 cM of any one of SEQ ID NO: 1, SEQ ID NO: 3, SEQ ID NO: 5, SEQ ID NO: 7, or SEQ ID NO: 9, b) identifying or selecting a plant if any of the said markers are present, as a melon (*Cucumis melo* spp. *melo*) plant that is resistant to ToLCNDV; and c) optionally verifying if the plant is resistant against ToLCNDV.

The invention also relates to a method for the production of a melon (*Cucumis melo* spp. *melo*) plant which is resistant against Tomato Leaf Curl New Delhi virus (ToLCNDV), said method which may comprise:

a) crossing a plant of the invention with a plant not which may comprise QTL-1, to obtain an F1 population;

b) optionally performing one or more rounds of selfing and/or crossing a plant from the F1 to obtain a further generation population;

c) selecting from the population a plant that may comprise QTL-1 and is resistant against Tomato Leaf Curl New Delhi virus (ToLCNDV), suitably by using a molecular marker linked to QTL-1. The plant can also be phenotypically selected for having resistance to ToLCNDV.

Representative seed of a plant of the invention was deposited as NCIMB 42705.

The invention further relates to a method for the production of a melon (*Cucumis melo* spp. *melo*) plant which is resistant against Tomato Leaf Curl New Delhi virus (ToLCNDV), said method which may comprise:

a) crossing a plant of the invention which may comprise QTL-1, with another melon parent plant not which may comprise QTL-1, to obtain an F1 population;

b) optionally selfing an F1 plant to obtain an F2 population;

c) backcrossing an F1 or an F2 plant with the preferred parent to obtain a BC1 population; and d) optionally selfing a BC1 plant to obtain a BC1F2 population;

e) selecting in the BC1 or the BC1F2 for a melon plant that may comprise QTL-1 and is resistant against Tomato Leaf Curl New Delhi virus (ToLCNDV), suitably by using a molecular marker linked to QTL-1. The plant can also be phenotypically selected for having resistance to ToLCNDV. The backcrossing, selfing and selection steps my optionally be repeated one to ten more times to produce further backcross progeny which may comprise QTL-1 and which is resistant against ToLCNDV.

Representative seed of a plant of the invention was deposited as NCIMB 42705.

In one embodiment of the invention, the plant of the invention used in the above methods for the production of a melon (*Cucumis melo* spp. *melo*) plant which is resistant against Tomato Leaf Curl New Delhi virus (ToLCNDV) is a plant grown from seed deposited under NCIMB accession number 42705.

The invention additionally provides for a method of introducing another desired trait into a melon (*Cucumis melo* spp. *melo*) plant which may comprise resistance to ToLCNDV, which may comprise:

a) crossing a melon (*Cucumis melo* spp. *melo*) plant of the invention with a second melon (*Cucumis melo* spp. *melo*) plant that may comprise the other desired trait to produce F1 progeny;

b) selecting an F1 progeny that may comprise QTL-1 and the other desired trait;

c) crossing the selected F1 progeny with either parent, to produce backcross progeny;

d) selecting backcross progeny which may comprise QTL-1 and the other desired trait; and e) optionally repeating steps c) and d) one or more times in succession to produce selected fourth or higher backcross progeny that may comprise the other desired trait and has resistance to ToLCNDV.

Representative seed of a plant of the invention was deposited as NCIMB 42705.

In one embodiment of the invention, the plant of the invention used in the method of introducing another desired trait into a melon (*Cucumis melo* spp. *melo*) plant which may comprise resistance to ToLCNDV is a plant grown from seed deposited under NCIMB accession number 42705.

Optionally, selfing steps are performed after any of the crossing or backcrossing steps. Selection of a plant which may comprise QTL-1 of the invention and the other desired trait can alternatively be done following any crossing or selfing step of the method. The desired trait can be selected from, but is not limited to, the following group: resistance to bacterial, fungal or viral diseases, insect or pest resistance, improved germination, plant size, plant type, improved shelf-life, water stress and heat stress tolerance, and male sterility. The invention includes a melon (*Cucumis melo* spp. *melo*) plant produced by this method and the melon (*Cucumis melo* spp. *melo*) fruit obtained therefrom.

The invention further relates to a method for the production of a melon (*Cucumis melo* spp. *melo*) plant which may comprise QTL-1 that leads to resistance to ToLCNDV, by using tissue culture of plant material that may comprise QTL-1 in its genome.

The invention further relates to a method for the production of a melon (*Cucumis melo* spp. *melo*) plant which may comprise QTL-1 that leads to resistance to ToLCNDV, by using vegetative reproduction of plant material that may comprise QTL-1 in its genome.

The invention further provides a method for the production of a melon (*Cucumis melo* spp. *melo*) plant having resistance to ToLCNDV as defined herein by using a doubled haploid generation technique to generate a doubled haploid line that homozygously may comprise QTL-1 and is resistant against ToLCNDV.

The invention further relates to a method for the production of a melon (*Cucumis melo* spp. *melo*) plant which may comprise QTL-1 wherein said QTL-1 leads to ToLCNDV resistance, which method may comprise growing a seed which may comprise QTL-1 into the said melon (*Cucumis melo* spp. *melo*) plant. In one embodiment, the seed of the method is seed deposited with the NCIMB under deposit number 42705, or progeny seed thereof.

The invention further relates to a method for seed production which may comprise growing melon (*Cucumis melo* spp. *melo*) plants from seeds of the invention, allowing the plants to produce fruits with seeds, and harvesting those seeds. Production of the seeds is suitably done by crossing or selfing. Preferably the seeds that are so produced have the capability to grow into plants that are resistant to ToLCNDV.

The invention further relates to hybrid seed and to a method for producing said hybrid seed, which may comprise crossing a first parent plant with a second parent plant and harvesting the resultant hybrid seed, wherein the first parent plant and/or the second parent plant is a plant of the invention. The resultant hybrid plant which may comprise QTL-1 of the invention and which exhibits resistance to ToLCNDV is also a plant of the invention.

It is clear that the parent that provides the trait of the invention is not necessarily a plant grown directly from the deposited seeds. The parent can also be a progeny plant from the seed or a progeny plant from seeds that are identified to have the trait of the invention by other means.

Introgression of QTL-1 as used herein means introduction of QTL-1 from a donor plant which may comprise said QTL-1 into a recipient plant not carrying said QTL-1 by standard breeding techniques wherein selection for plants which may comprise QTL-1 can be performed phenotypically by means of observation of the resistance to ToLCNDV, or selection can be performed with the use of markers through marker assisted breeding, or combinations of these. Selection is started in the F1 or any further generation from a cross between the recipient plant and the donor plant, suitably by using markers as identified herein. The skilled person is familiar with creating and using new molecular markers that can be used to identify or are linked to the trait of the invention. Development and use of such markers for identification and selection of plants of the invention is also part of the invention.

The phrase "trait" in the context of this application refers to the resistance phenotype of the cultivated melon plant. In particular, the word "trait" refers to the trait of the invention, more in particular to the resistance to ToLCNDV. When a cultivated melon plant exhibits the trait of the invention, its genome may comprise QTL-1 causing the trait of the invention. The cultivated melon plant thus may comprise QTL-1 of the invention. Hence, the "trait of the invention" as used herein is intended to refer to the trait of resistance to ToLCNDV.

As used herein a marker that is genetically "linked to" a QTL can be used for the identification of that QTL, when the recombination between the marker and the QTL, i.e. between marker and trait, is less than 5% in a segregating population resulting from a cross between a plant which may comprise the QTL and a plant lacking the QTL.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: ToLCNDV Resistance Testing of Plants and Fruits

GBN.20082 and S15E.99050032, an F1 plant resulting from a cross between GBN.20082 and Vedrantais were subjected to a ToLCNDV resistance test in order to identify new *C. melo* material with resistance to ToLCNDV. Plants of melon cultivars Vedrantais and Caribbean Gold were used as ToLCNDV susceptible controls. To assess whether a plant is resistant to ToLCNDV, plants were inoculated with ToLCNDV either mechanically or using whiteflies (*Bemisia tabaci*) as a natural vector.

(i) Mechanical Inoculation of Melon Plants

Twenty young plants of each genotype were mechanically inoculated with a ToLCNDV isolate that was initially obtained from an infected field in Almeria, Spain. Mechanical inoculation of ToLCNDV was performed using the method adapted from Lopez et al. 2015, such that the ToLCDNV inoculum was prepared using buffer (i) as described (Euphytica. 2015 (204): 679-691).

Five phenotypic assessments were performed on the plants at 2, 5, 9, 11 and 13 weeks after infection (wai), and herein named assessment 1, 2, 3, 4 and 5 respectively. Each plant was visually scored for the amount of ToLCNDV symptoms, based on the scale explained in Table 2.

TABLE 2

ToLCNDV Plant Disease Test

| Disease Score | ToLCNDV symptoms on plants | Resistance/ Susceptibility to ToLCNDV |
|---|---|---|
| 1 | No symptoms; healthy plant | Resistant |
| 2 | Some non-specific yellowing due to aging, maturation or yellowing not related to viral infection | Resistant |
| 3 | No leaf deformation, symptoms starting to develop; mainly on older leaves, some yellowing spots occur on less than 25% of the plant surface; re-growth and the top of the plant is symptomless | Intermediate resistant |
| 4 | No leaf deformation, yellowing symptoms, 25-50% of the plant affected; yellow spots are more abundant than score 3; re-growth and the top of the plant is symptomless | Susceptible |
| 5 | No leaf deformation, severe yellowing symptoms; up to 100% of the plant affected with yellow spots and areas where yellow spots have merged in the larger yellow areas; symptoms are progressive even in newly formed leaves | Susceptible |
| 6 | Yellowing symptoms and some mild leaf deformation symptoms occur; some shoots and younger leaves show some deformed parts; some minor mottling in restricted areas | Susceptible |
| 7 | Severe yellowing; strong deformation and mottling in older leaves; in the younger parts, emerging shoots and newly formed leaves show some milder deformation; up to 75% of the plant surface shows deformation; plant is still growing | Susceptible |
| 8 | Severe leaf deformation, entire plant affected; the plant starts producing micro leaves and will no longer grow | Susceptible |
| 9 | Extreme severe leaf deformation, entire plant affected. Plants are dwarfed, necrotic or even die | Susceptible |

The mean disease score for each genotype at each assessment was calculated. Pairwise comparison between genotypes per assessment was made using one-way ANOVA with Tukey's HSD (95% confidence level). Quantitative PCR (qPCR) may be used to confirm the ToLCNDV viral load in the inoculated plants. The skilled person is familiar with designing a qPCR assay that is specific for detecting and quantifying ToLCNDV.

(ii) Whitefly Inoculation of Melon Plants

At 5 wai, the mechanically inoculated plants from (i) were then randomized in a greenhouse alongside 20 healthy, uninfected plants of each genotype. Since these uninfected plants were sown at the same time as the plants used for the mechanical inoculation, all plants used in the ToLCNDV resistance test are thus at the same developmental age. Non-viruliferous whiteflies were then released into the greenhouse in order to mimic natural infection. Using the scale of Table 2, five phenotypic assessments were performed on the whitefly inoculated plants, twice before the whiteflies were released into the greenhouse and at 4, 6 and 8 wai, and herein named assessment 1, 2, 3, 4 and 5, respectively. It should be noted that due to the set-up of the test, disease symptoms in the whitefly inoculated plants were observable only from approximately 3 weeks after the release of the whiteflies into the greenhouse, but the symptoms reached the same severity as mechanically inoculated plants by 4 weeks after inoculation (i.e. by Assessment 3).

Each plant was scored for the amount of ToLCNDV disease symptoms, based on the scale explained in Table 2. The mean disease score for each genotype at each assessment was calculated. Pairwise comparison between genotypes per assessment was made using one-way ANOVA with Tukey's HSD (95% confidence level). Quantitative PCR (qPCR) may be used to confirm the ToLCNDV viral load in the inoculated plants. The skilled person is familiar with designing a qPCR assay that is specific for detecting and quantifying ToLCNDV.

Figure 1:
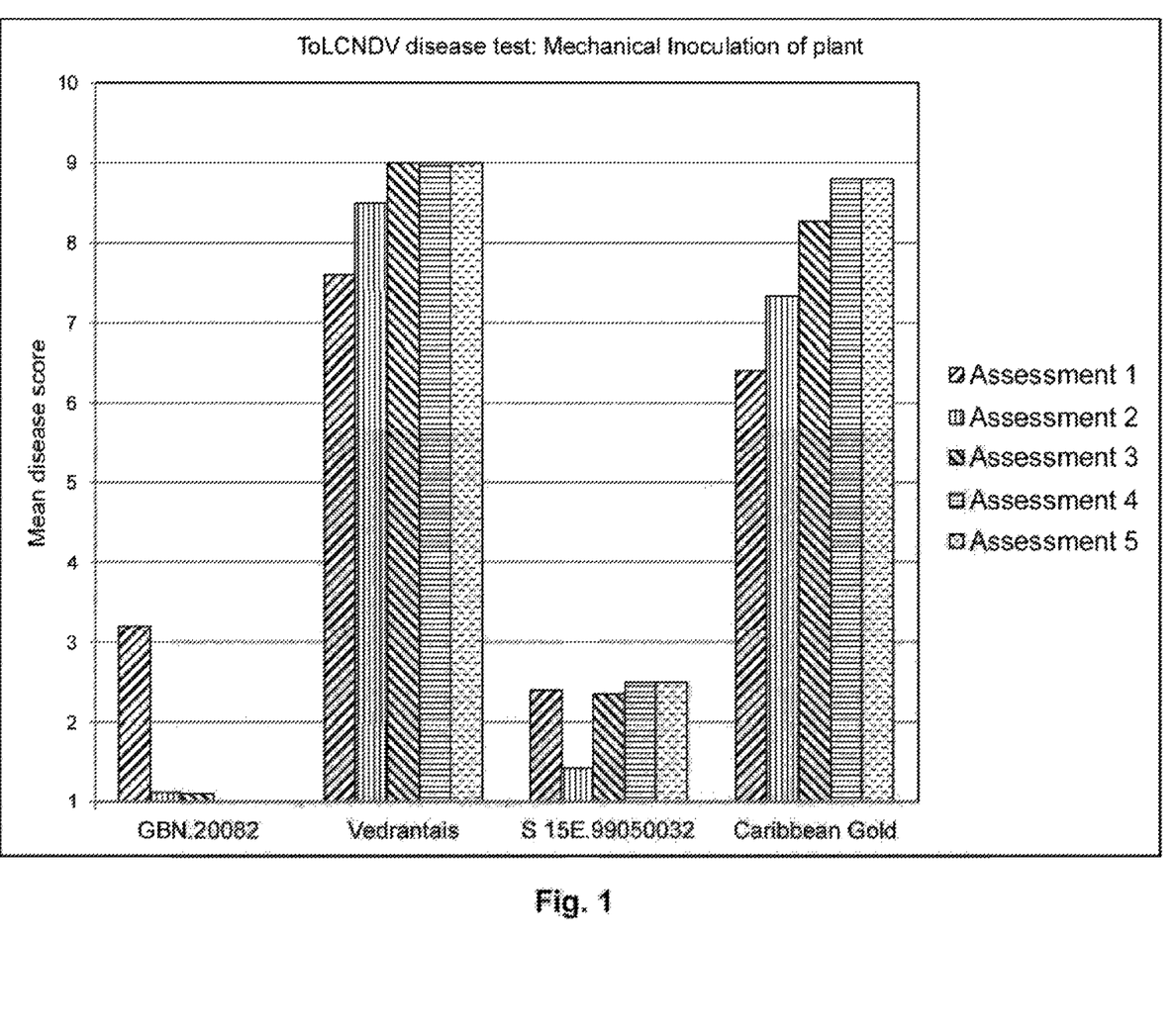
FIG. 1 depicts a ToLCNDV disease test: Mechanical Inoculation of plant.

The results of the ToLCNDV disease test of the mechanically inoculated melon plants in the trial are shown in FIG. 1 and Table 3. It is clear from the results that GBN.20082 provides the highest level of resistance against ToLCNDV. S15E.9905, having GBN.20082 as one of its parents, also has a high level of resistance against ToLCNDV. The other parent of S15E.9905, Vedrantais, is highly susceptible to ToLCNDV, as is Caribbean Gold. qPCR (results not shown) confirmed that GBN.20082 and S15E.9905 had low concentrations of ToLCNDV as compared to Vedrantais and Caribbean Gold. Furthermore, GBN.20082 had a lower concentration of ToLCNDV as compared to S15E.9905.

TABLE 3

| Pairwise comparison* | Assessment 1 | Assessment 2 | Assessment 3 | Assessment 4 | Assessment 5 |
|---|---|---|---|---|---|
| GBN.20082 | 3.2 a | 1.118 a | 1.1 a | 1 a | 1 a |
| Vedrantais | 7.6 b | 8.5 b | 9 b | 9 b | 9 b |
| S15E.99050032 | 2.4 a | 1.421 a | 2.35 a | 2.5 a | 2.5 a |
| Caribbean Gold | 6.4 b | 7.333 b | 8.263 b | 8.8 b | 8.8 b |

*lower case letters denote statistically significant differences between genotypes per assessment using one-way ANOVA with Tukey's HSD (95% confidence level)

Figure 2:
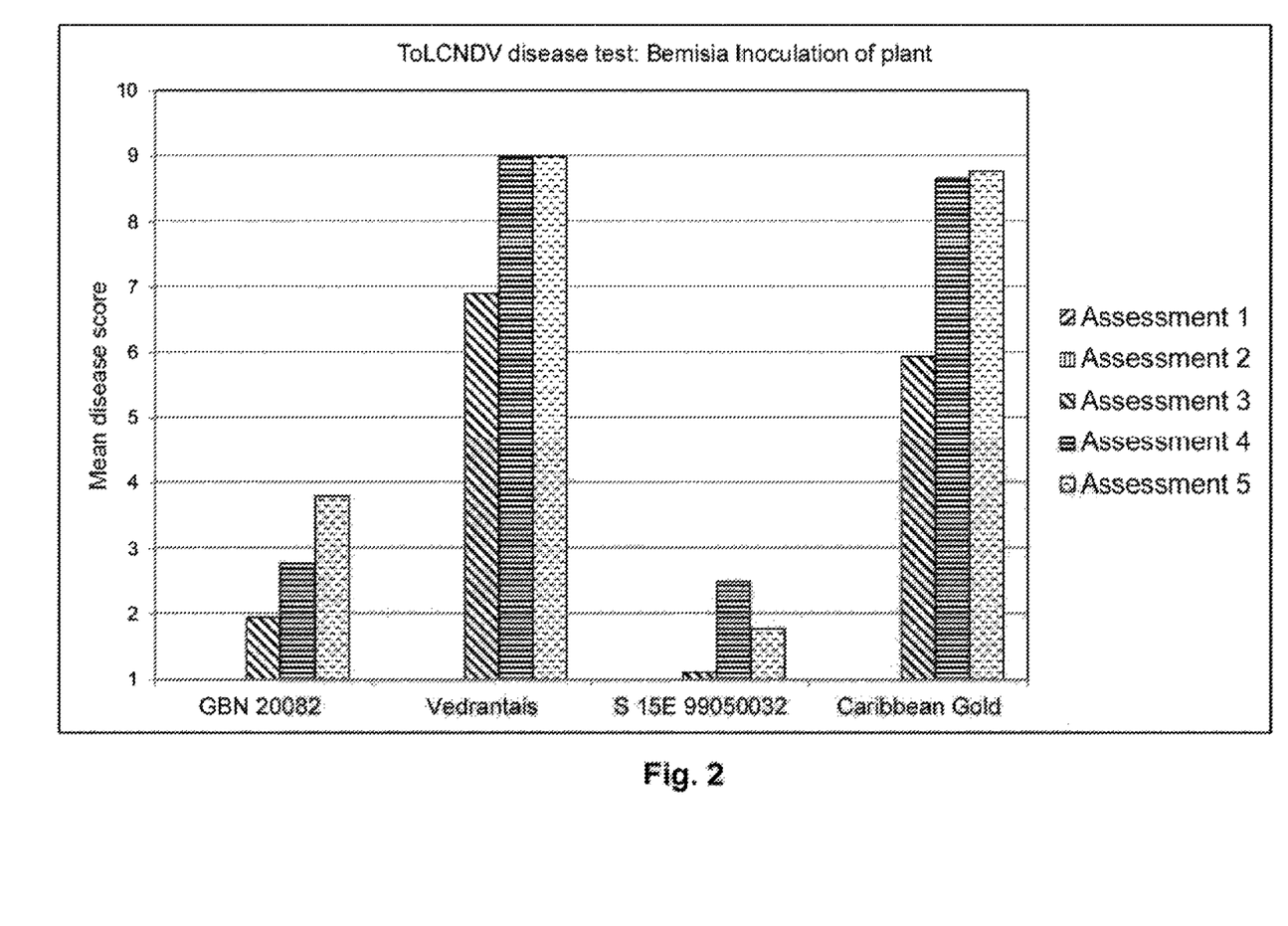
FIG. 2 depicts a ToLCNDV disease test: *Bemisia* Inoculation of plant.

The results of the ToLCNDV disease test of the whitefly inoculated melon plants in the trial are shown in FIG. 2 and Table 4. Compared to Vedrantais and Caribbean Gold, both GBN.20082 and S15E.99050032 provide a good level of resistance against ToLCNDV. Vedrantais and Caribbean Gold are susceptible to ToLCNDV. qPCR (results not shown) confirmed that 20 GBN.20082 and S15E.9905 had low concentrations of ToLCNDV as compared to Vedrantais and Caribbean Gold. Furthermore, GBN.20082 had a lower concentration of ToLCNDV as compared to S15E.9905.

TABLE 4

| Pairwise comparison* | Assessment 1 | Assessment 2 | Assessment 3 | Assessment 4 | Assessment 5 |
|---|---|---|---|---|---|
| GBN.20082 | 1 a | 1 a | 1.952 a | 2.778 a | 3.8 a |
| Vedrantais | 1 a | 1 a | 6.905 b | 9 b | 9 b |
| S15E.99050032 | 1 a | 1 a | 1.111 a | 2.5 a | 1.778 a |
| Caribbean Gold | 1 a | 1 a | 5.947 b | 8.667 b | 8.778 b |

*lower case letters denote statistically significant differences between genotypes per assessment using one-way ANOVA with Tukey's HSD (95% confidence level)

Given the results from the two different inoculation methods of the ToLCNDV disease test in (i) and (ii), it can be concluded that both methods of inoculation are comparable and either method can suitably be used for testing melon plants in a ToLCNDV disease test. Additionally, the results indicate that the ToLCNDV resistance of GBN.20082 appears to be heritable in a partially dominant manner since S15E.9905 is ToLCNDV resistant.

(iii) Assessment of ToLCNDV Symptoms on Melon Fruit of Mechanically and *Bemisia* Inoculated Plants In addition to disease testing of the melon plant, melon fruits that were produced by the plants that were either mechanically or whitefly inoculated with ToLCNDV from (i) and (ii) were also observed for ToLCNDV disease symptoms. Three phenotypic assessments were performed on the fruits at 9, 11 and 13 wai of the mechanically inoculated plants and at 4, 6 and 8 wai of the whitefly inoculated plants, and herein named assessment 1, 2, and 3, respectively.

Fruits were visually scored for the amount of ToLCNDV disease symptoms, based on the scale shown in Table 5. The mean disease score for each genotype at each assessment was calculated. Pairwise comparison between genotypes per assessment was made using one-way ANOVA with Tukey's HSD (95% confidence level).

TABLE 5

ToLCNDV Fruit Disease Symptoms

| Disease score | ToLCNDV symptoms on melon fruits |
|---|---|
| 0 | Fruit present. No symptoms observed on fruit. |
| 1 | Fruit present. Slight net cracking observed on fruit. |
| 2 | Fruit present. Clear ToLCNDV symptoms observed on fruit: lesions or deep net cracking |
| 3 | Fruit present. Strong ToLCNDV symptoms observed on fruit: heavy cracks and fruit deformation. |

Figure 3:
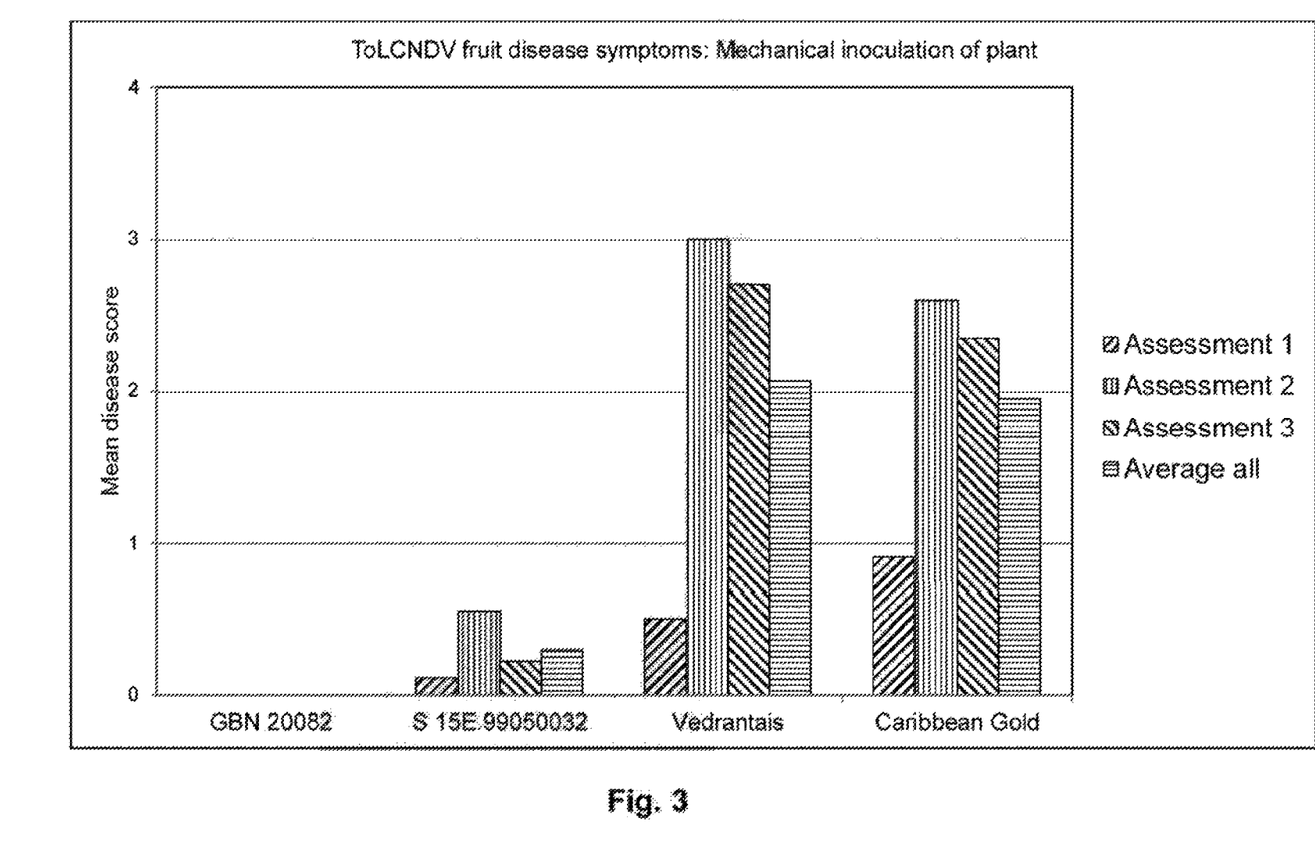
FIG. 3 depicts a ToLCNDV fruit disease symptoms: Mechanical inoculation of plant.
Figure 4:
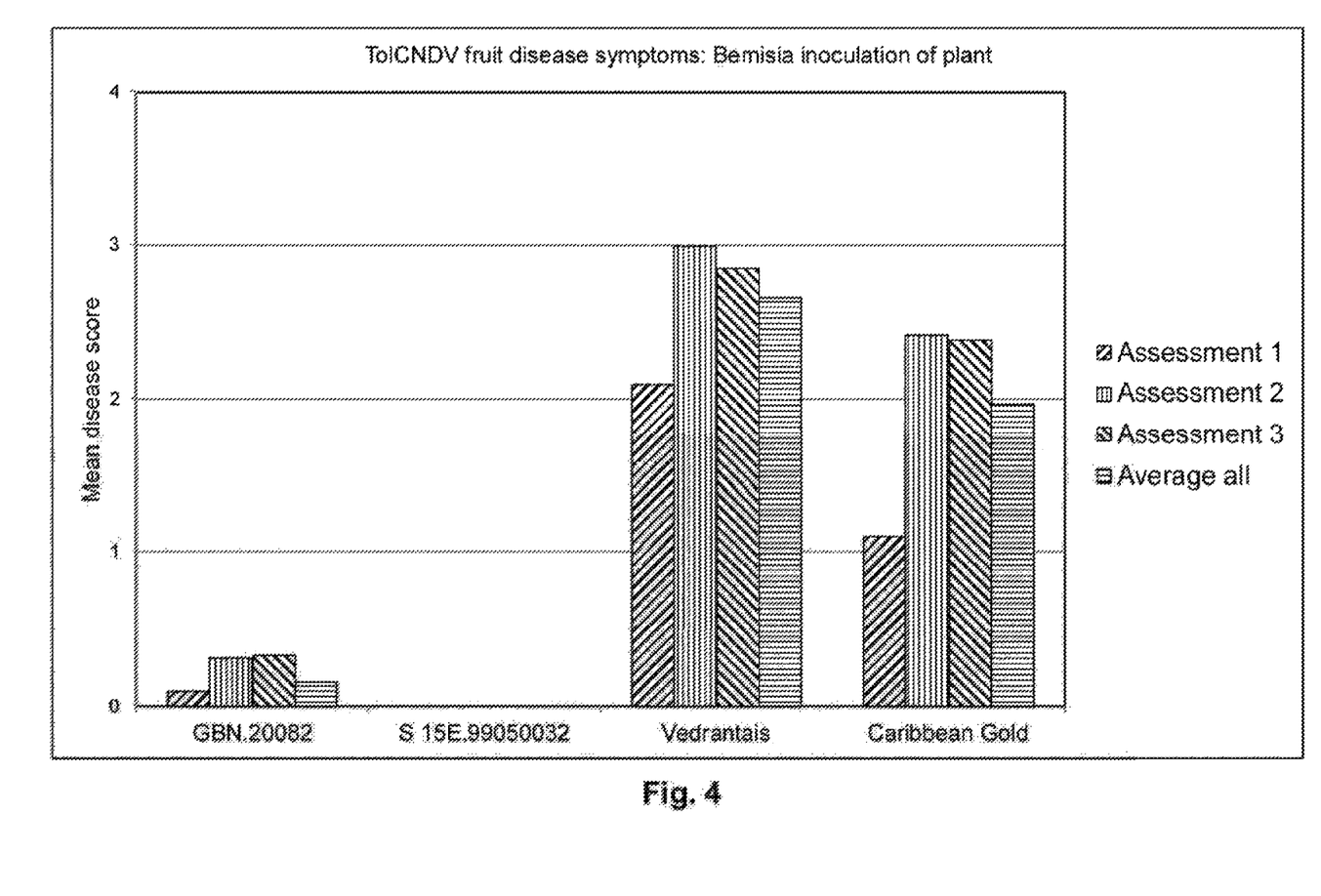
FIG. 4 depicts a TolCNDV fruit disease symptoms: *Bemisia* inoculation of plant.

The results of the assessment of ToLCNDV fruit disease symptoms of the mechanically inoculated melon plants are shown in FIG. 3 and Table 6, and the assessment of ToLCNDV fruit disease symptoms of the whitefly inoculated melon plants are shown in FIG. 4 and Table 7. Regardless of the ToLCNDV inoculation method utilized, fruits produced by both GBN.20082 and S15E.99050032 do not present clear ToLCNDV symptoms, whereas the fruits produced by Vedrantais and Caribbean Gold clearly present ToLCNDV symptoms. These observations taken together with the results of the ToLCNDV plant disease test, reinforce that the resistance of the invention is heritable and is inherited in a partial dominant manner.

TABLE 6

| Pairwise comparison* | Assessment 1 | Assessment 2 | Assessment 3 | Average all assessments |
|---|---|---|---|---|
| GBN.20082 | 0 a | 0 a | 0 a | 0 a |
| S15E.99050032 | 0.1111 a | 0.55 a | 0.2222 a | 0.2944 a |
| Vedrantais | 0.5 ab | 3 b | 2.7059 b | 2.0686 b |
| Caribbean Gold | 0.9091 b | 2.6 b | 2.35 b | 1.9530 b |

*lower case letters denote statistically significant differences between genotypes per assessment using one-way ANOVA with Tukey's HSD (95% confidence level)

TABLE 7

| Pairwise comparison* | Assessment 1 | Assessment 2 | Assessment 3 | Average all assessments |
|---|---|---|---|---|
| GBN.20082 | 0.1 a | 0.3158 a | 0.3333 a | 0.1587 a |
| S15E.99050032 | 0 a | 0 a | 0 a | 0 a |
| Vedrantais | 2.1 b | 3 b | 2.8571 b | 2.6667 b |
| Caribbean Gold | 1.1053 b | 2.4211 b | 2.3889 b | 1.9717 b |

*lower case letters denote statistically significant differences between genotypes per assessment using one-way ANOVA with Tukey's HSD (95% confidence level)

Example 2: Mapping of QTL-1

In order to map the ToLCNDV resistance conferring QTL of the invention, 78 recombinant inbred lines (RIL) derived by single seed descent (SSD) from a cross between Vedrantais (ToLCNDV susceptible parent) and GBN.20082 (ToLCNDV resistant parent) were used for QTL mapping. The RIL population and parental lines were phenotyped for resistance to ToLCNDV. In this trial, the scores ranged from very resistant (1) to very susceptible (5). Per individual line, 4 replicates each consisting of 5 plants, were scored at two time points for ToLCNDV resistance. Parental lines were also scored in the same way. For QTL mapping, the average of the 4 replicates per individual line was calculated and used as input for the mapping.

Genotype data for 78 individuals of the population and parental lines were obtained using 629 SNP markers. Quality control of genotype data was performed using tools available in the R/qtl software package. Non-polymorphic markers, strong segregation distortion and plants or markers with excess of missing data were removed. Following data clean up, 370 markers remained and could be used for mapping. Each of the 370 markers were given one of three scores per plant: AA for homozygous resulting from Vedrantais, BB for homozygous resulting from GBN.20082, and H for the heterozygotes.

Linkage groups were defined using pairwise linkage information between markers. Marker order was determined. Linkage group orientation and naming was corrected based on the publicly available *C. melo* genome reference sequence cm_DHL92_v3.5 (access to version 3.5 available at melonomics.net). A good linkage map was obtained covering all 12 chromosomes of *C. melo* with the lowest coverage for chromosome 10 which had only 9 markers, and the highest for chromosomes 11, represented by 43 markers.

QTL analysis was performed using R and the R/qtl software package. Trait distributions, outliers and correlations were studied, after which StepWise QTL analysis was executed. Mapping of the data resulted in the identification of a QTL on chromosome 11. This QTL is further indicated as QTL-1. The markers that resulted from the QTL analysis as flanking QTL-1 on chromosome 11 are indicated with SEQ ID NO: 1 and SEQ ID NO: 9. It should be noted that while markers with SEQ ID NO: 1 and SEQ ID NO: 9 flank QTL-1, they are also linked to the QTL.

The mapping of this population also resulted in the identification of a number of polymorphic SNP markers that can be used to identify the presence of QTL-1 on chromosome 11. The SNP markers resulting from mapping of this population are indicated as SEQ ID Nos. 3, 5, and 7. The sequence of these markers, as well as their genetic position on the genetic map and corresponding physical positions on the publicly available *C. melo* genome reference sequence cm_DHL92_v3.5 are listed in Table 1. Thus, these markers may be used to identify individuals of other populations that comprise QTL-1 on chromosome 11 in their genome.

In the deposit NCIMB 42705, the presence of QTL-1 and the ToLCNDV resistant genotype is linked to SNP markers with SEQ ID NO: 1, SEQ ID NO: 3, SEQ ID NO: 5, SEQ ID NO: 7, and SEQ ID NO: 9. These SNP sequences can be used as molecular markers for identifying ToLCNDV resistant plants grown from said deposit. Furthermore, since the markers were also positioned on the melon public genome map and the actual physical positions determined (Table 1), these markers may be used to identify the presence of QTL-1 on chromosome 11 in any other population that comprises said QTL-1.

The sequences of SEQ ID NO: 2, SEQ ID NO: 4, SEQ ID NO: 6, SEQ ID NO: 8, and SEQ ID NO: 10 represent the ToLCNDV susceptible wildtype melon (*C. melo* spp. *melo*) sequences for the molecular SNP markers of SEQ ID NO: 1, SEQ ID NO: 3, SEQ ID NO: 5, SEQ ID NO: 7, and SEQ ID NO: 9, respectively.

The invention is further described by the following numbered paragraphs:

1. A melon (*Cucumis melo* spp. *melo*) plant resistant against Tomato Leaf Curl New Delhi virus (ToLCNDV), wherein the plant comprises QTL-1 in its genome, which QTL-1 confers resistance to Tomato Leaf Curl New Delhi virus (ToLCNDV) and is present in a plant grown from a seed deposited under NCIMB accession number 42705.

2. The melon plant of paragraph 1, wherein QTL-1 is located on chromosome 11, between the marker sequences SEQ ID NO: 1 and SEQ ID NO: 9.

3. The melon plant of paragraph 1 or 2, wherein QTL-1 is linked to one or more markers selected from the group consisting of SEQ ID NO: 1, SEQ ID NO: 3, SEQ ID NO: 5, SEQ ID NO: 7, and SEQ ID NO: 9, or any combination thereof.

4. The melon plant of any one of the paragraphs 1 to 3, wherein QTL-1 can be identified by one or more markers selected from the group consisting of SEQ ID NO: 1, SEQ ID NO: 3, SEQ ID NO: 5, SEQ ID NO: 7, and SEQ ID NO: 9, or any combination thereof.

5. A melon seed comprising QTL-1 in its genome, wherein QTL-1 is as defined in any one of the paragraphs 1 to 4.

6. The melon seed of paragraph 5, wherein the plant grown from said seed is resistant against ToLCNDV.

7. A progeny of the melon plant of any one of the paragraphs 1 to 4, or progeny of the melon plant grown from seed of paragraphs 5 or 6, wherein the progeny comprises QTL-1 as defined in any one of the paragraphs 1 to 4.

8. The progeny of paragraph 7, wherein the progeny is resistant against ToLCNDV.

9. A melon fruit harvested from a plant of any one of the paragraphs 1 to 4 or from a plant grown from a seed of paragraph 5 or paragraph 6.

10. The melon fruit of paragraph 9, wherein the melon fruit comprises QTL-1 in its genome.

11. The melon fruit of paragraphs 9 or 10, wherein the melon fruit is resistant against ToLCNDV.

12. A food product or a processed food product comprising the melon fruit or part thereof of any one of the paragraphs 9 to 11.

13. A cell of a melon (*Cucumis melo* spp. *melo*) plant resistant against ToLCNDV, which cell comprises the QTL-1 as defined in any one of the paragraphs 1 to 4.

14. Tissue culture of a melon (*Cucumis melo* spp. *melo*) plant resistant against ToLCNDV, which tissue culture comprises the QTL-1 as defined in any one of the paragraphs 1 to 4.

15. Propagation material suitable for producing a melon (*Cucumis melo* spp. *melo*) plant of any one of the paragraphs 1 to 4, wherein the propagation material is suitable for sexual reproduction, and is in particular selected from a microspores, pollen, ovary, ovule, embryo sac and egg cell, or is suitable for vegetative reproduction, and is in particular selected from a cutting, root, stems cell, protoplast, or is suitable for tissue cultures of regenerable cells, and is in particular selected from a leaf, pollen, embryo, cotyledon, hypocotyl, meristematic cell, root, root tip, anther, flower, seed and stem, and wherein the plant produced from the propagation material comprises the QTL-1 as defined in any one of the paragraphs 1 to 4.

16. A marker for the identification of QTL-1, wherein QTL-1 when present in the genome of a melon (*Cucumis melo* spp. *melo*) plant confers resistance to ToLCNDV, which marker is selected from the group consisting of SEQ ID NO: 1, SEQ ID NO: 3, SEQ ID NO: 5, SEQ ID NO: 7, and SEQ ID NO: 9, or any combination thereof.

17. Use of the marker of paragraph 16 to identify or develop a ToLCNDV resistant melon (*Cucumis melo* spp. *melo*) plant, or develop additional marker(s) linked to QTL-1, which when present in the genome of a melon (*Cucumis melo* spp. *melo*) plant confers resistance to ToLCNDV.

18. A method of testing a melon (*Cucumis melo* spp. *melo*) plant for the presence of QTL-1 in its genome, comprising detecting a marker sequence selected from the group consisting of SEQ ID NO: 1, SEQ ID NO: 3, SEQ ID NO: 5, SEQ ID NO: 7, and SEQ ID NO: 9, or any combination thereof, in the genome of the melon (*Cucumis melo* spp. *melo*) plant.

19. The method of paragraph 18, further comprising selecting a melon (*Cucumis melo* spp. *melo*) plant that comprises QTL-1 in its genome.

20. A method for identifying or selecting a melon (*Cucumis melo* spp. *melo*) plant which is resistant against Tomato Leaf Curl New Delhi virus (ToLCNDV), said method comprising:

a) assaying genomic nucleic acids of a melon (*Cucumis melo* spp. *melo*) plant for the presence of a genomic marker genetically linked to QTL-1, wherein QTL-1 is associated with ToLCNDV resistance, wherein said QTL-1 is within 20 cM or 10 cM or 5 cM of any one of the markers SEQ ID NO: 1, SEQ ID NO: 3, SEQ ID NO: 5, SEQ ID NO: 7, or SEQ ID NO: 9;

b) identifying or selecting a plant if any of the said markers are present, as a melon (*Cucumis melo* spp. *melo*) plant that is resistant to ToLCNDV; and c) optionally verifying if the plant is resistant against ToLCNDV.

21. A method for producing a melon (*Cucumis melo* spp. *melo*) plant which is resistant against Tomato Leaf Curl New Delhi virus (ToLCNDV), said method comprising:

a) crossing a plant of any one of the paragraphs 1 to 4 with another plant to
obtain an F1 population;

b) optionally performing one or more rounds of selfing and/or crossing a plant from the F1 to obtain a further generation population;

c) selecting from the population a plant that comprises QTL-1 and is resistant against Tomato Leaf Curl New Delhi virus (ToLCNDV).

22. The method of paragraph 21, wherein the plant of any one of the paragraphs 1 to 4 is a plant grown from seed deposited under NCIMB accession number 42705, or progeny thereof comprising QTL-1 in its genome.

23. A method for producing a melon (*Cucumis melo* spp. *melo*) plant which is resistant against Tomato Leaf Curl New Delhi virus (ToLCNDV), said method comprising growing a plant which comprises the QTL-1 as defined in any one of the paragraphs 1 to 4.

24. The method of paragraph 23, wherein the plant is a plant grown from seed deposited under NCIMB accession number 42705, or progeny thereof comprising QTL-1 in its genome.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A melon (*Cucumis melo* spp. *melo*) plant resistant against Tomato Leaf Curl New Delhi virus (ToLCNDV), wherein the plant comprises QTL-1 in its genome, which QTL-1 confers resistance to Tomato Leaf Curl New Delhi virus (ToLCNDV) and is present in a plant grown from a seed deposited under NCIMB Accession No. 42705, wherein QTL-1 is located on chromosome 11, between the marker sequences SEQ ID NO: 1 and SEQ ID NO: 9.

2. The melon plant as claimed in claim 1, wherein QTL-1 is linked to one or more markers selected from the group consisting of SEQ ID NO: 1, SEQ ID NO: 3, SEQ ID NO: 5, SEQ ID NO: 7, and SEQ ID NO: 9, or any combination thereof.

3. The melon plant as claimed in claim 1, wherein QTL-1 can be identified by one or more markers selected from the group consisting of SEQ ID NO: 1, SEQ ID NO: 3, SEQ ID NO: 5, SEQ ID NO: 7, and SEQ ID NO: 9, or any combination thereof.

4. A melon seed comprising QTL-1 in its genome, wherein QTL-1 is as defined in claim 1.

5. The melon seed as claimed in claim 4, wherein the plant grown from said seed is resistant against ToLCNDV.

6. A progeny of the melon plant as claimed in claim 1, or progeny of the melon plant grown from seed as claimed in claim 4, wherein the progeny comprises QTL-1 as defined in claim 1.

7. The progeny as claimed in claim 6, wherein the progeny is resistant against ToLCNDV.

8. A melon fruit harvested from a plant as claimed in claim 1 or from a plant grown from a seed as claimed in claim 4.

9. The melon fruit as claimed in claim 8, wherein the melon fruit comprises QTL-1 in its genome.

10. The melon fruit as claimed in claim 8, wherein the melon fruit is resistant against ToLCNDV.

11. A food product or a processed food product comprising the melon fruit or part thereof as claimed in claim 8.

12. A cell of a melon (*Cucumis melo* spp. *melo*) plant resistant against ToLCNDV, which cell comprises the QTL-1 as defined in claim 1.

13. A tissue culture of a melon (*Cucumis melo* spp. *melo*) plant resistant against ToLCNDV, which tissue culture comprises the QTL-1 as defined in claim 1.

14. A propagation material suitable for producing a melon (*Cucumis melo* spp. *melo*) plant as claimed in claim 1,
wherein the propagation material is suitable for sexual reproduction, and is in particular selected from a microspores, pollen, ovary, ovule, embryo sac and egg cell, or is suitable for vegetative reproduction, and is in particular selected from a cutting, root, stem cell, protoplast, or is suitable for tissue cultures of regenerable cells, and is in particular selected from a leaf, pollen, embryo, cotyledon, hypocotyl, meristematic cell, root, root tip, anther, flower, seed and stem, and
wherein the plant produced from the propagation material comprises the QTL-1 as defined claim 1.

15. A marker for the identification of QTL-1, wherein QTL-1 when present in the genome of a melon (*Cucumis melo* spp. *melo*) plant confers resistance to ToLCNDV, which marker is selected from the group consisting of SEQ ID NO: 1, SEQ ID NO: 3, SEQ ID NO: 5, SEQ ID NO: 7, and SEQ ID NO: 9, or any combination thereof.

16. A method of testing a melon (*Cucumis melo* spp. *melo*) plant for the presence of QTL-1 in its genome, comprising detecting a marker sequence selected from the group consisting of SEQ ID NO: 1, SEQ ID NO: 3, SEQ ID NO: 5, SEQ ID NO: 7, and SEQ ID NO: 9, or any combination thereof, in the genome of the melon (*Cucumis melo* spp. *melo*) plant.

17. The method as claimed in claim 16, further comprising selecting a melon (*Cucumis melo* spp. *melo*) plant that comprises QTL-1 in its genome.

18. A method for identifying or selecting a melon (*Cucumis melo* spp. *melo*) plant which is resistant against Tomato Leaf Curl New Delhi virus (ToLCNDV), said method comprising:
  a) assaying genomic nucleic acids of a melon (*Cucumis melo* spp. *melo*) plant for the presence of a genomic marker genetically linked to QTL-1, wherein QTL-1 is associated with ToLCNDV resistance, wherein said QTL-1 is within 20 cM or 10 cM or 5 cM of any one of the markers SEQ ID NO: 1, SEQ ID NO: 3, SEQ ID NO: 5, SEQ ID NO: 7, or SEQ ID NO: 9;
  b) identifying or selecting a plant if any of the said markers SEQ ID NO: 1, SEQ ID NO: 3, SEQ ID NO: 5, SEQ ID NO: 7, or SEQ ID NO: 9 are present, as a melon (*Cucumis melo* spp. *melo*) plant that is resistant to ToLCNDV; and
  c) optionally verifying if the plant is resistant against ToLCNDV.

19. A method for producing a melon (*Cucumis melo* spp. *melo*) plant which is resistant against Tomato Leaf Curl New Delhi virus (ToLCNDV), said method comprising:
  a) crossing a plant as claimed in claim 1 with another plant to obtain an F1 population;
  b) optionally performing one or more rounds of selfing and/or crossing a plant from the F1 to obtain a further generation population; and
  c) selecting from the population a plant that comprises QTL-1 and is resistant against Tomato Leaf Curl New Delhi virus (ToLCNDV).

20. The method as claimed in claim 19, wherein the plant as claimed in claim 1 is a plant grown from seed deposited under NCIMB Accession No. 42705, or progeny thereof comprising QTL-1 in its genome.

21. A method for producing a melon (*Cucumis melo* spp. *melo*) plant which is resistant against Tomato Leaf Curl New Delhi virus (ToLCNDV), said method comprising growing a plant which comprises the QTL-1 as defined in claim 1.

22. The method as claimed in claim 21, wherein the plant is a plant grown from seed deposited under NCIMB Accession No. 42705, or progeny thereof comprising QTL-1 in its genome.

\* \* \* \* \*

UNITED STATES PATENT AND TRADEMARK OFFICE
CERTIFICATE OF CORRECTION

PATENT NO. : 11,130,963 B2
APPLICATION NO. : 16/691059
DATED : September 28, 2021
INVENTOR(S) : Florian Müller et al.

It is certified that error appears in the above-identified patent and that said Letters Patent is hereby corrected as shown below:

In the Claims

Column 27, Line 1, Claim 18 should read as follows:
A method for identifying or selecting a melon (Cucumis melo spp. melo) plant which is resistant against Tomato Leaf Curl New Delhi virus (ToLCNDV), said method comprising: a) assaying genomic nucleic acids of a melon (Cucumis melo spp. melo) plant for the presence of a genomic marker genetically linked to QTL-1, wherein QTL-1 is associated with ToLCNDV resistance, wherein said QTL-1 is within 20 cM or 10 cM or 5 cM of any one of the markers SEQ ID NO: 1, SEQ ID NO: 3, SEQ ID NO: 5, SEQ ID NO: 7, or SEQ ID NO: 9; b) identifying or selecting a plant if any of the markers SEQ ID NO: 1, SEQ ID NO: 3, SEQ ID NO: 5, SEQ ID NO: 7, or SEQ ID NO: 9 are present, as a melon (Cucumis melo spp. melo) plant that is resistant to ToLCNDV; and c) optionally verifying if the plant is resistant against ToLCNDV.

Signed and Sealed this
Tenth Day of May, 2022

Katherine Kelly Vidal
*Director of the United States Patent and Trademark Office*